(12) United States Patent
Glazer

(10) Patent No.: US 10,849,913 B2
(45) Date of Patent: Dec. 1, 2020

(54) COMPOSITIONS AND METHODS FOR THE TREATMENT OF SKIN LESIONS

(71) Applicant: Scott David Glazer, Northbrook, IL (US)

(72) Inventor: Scott David Glazer, Northbrook, IL (US)

(73) Assignee: Scott David Glazer, Northbrook, IL (US)

( * ) Notice: Subject to any disclaimer, the term of this patent is extended or adjusted under 35 U.S.C. 154(b) by 80 days.

(21) Appl. No.: 16/183,502

(22) Filed: Nov. 7, 2018

(65) Prior Publication Data

US 2019/0134063 A1    May 9, 2019

Related U.S. Application Data

(60) Provisional application No. 62/583,979, filed on Nov. 9, 2017.

(51) Int. Cl.

| | |
|---|---|
| *A61K 31/59* | (2006.01) |
| *A61K 31/513* | (2006.01) |
| *A61K 31/195* | (2006.01) |
| *A61K 9/107* | (2006.01) |
| *A61K 9/00* | (2006.01) |
| *A61K 47/18* | (2017.01) |
| *A61P 35/00* | (2006.01) |
| *A61K 47/14* | (2017.01) |
| *A61K 47/26* | (2006.01) |
| *A61K 47/10* | (2017.01) |
| *A61P 17/00* | (2006.01) |
| *A61K 31/196* | (2006.01) |
| *A61K 31/593* | (2006.01) |
| *A61K 45/06* | (2006.01) |

(52) U.S. Cl.
CPC ............ *A61K 31/59* (2013.01); *A61K 9/0014* (2013.01); *A61K 9/107* (2013.01); *A61K 31/195* (2013.01); *A61K 31/196* (2013.01); *A61K 31/513* (2013.01); *A61K 31/593* (2013.01); *A61K 45/06* (2013.01); *A61K 47/10* (2013.01); *A61K 47/14* (2013.01); *A61K 47/18* (2013.01); *A61K 47/26* (2013.01); *A61P 17/00* (2018.01); *A61P 35/00* (2018.01)

(58) Field of Classification Search
CPC .... A61K 31/59; A61K 31/593; A61K 31/513; A61K 31/196; A61K 9/0014
See application file for complete search history.

(56) References Cited

FOREIGN PATENT DOCUMENTS

WO    2016/040638 A2    3/2016

OTHER PUBLICATIONS

Kim, R.H. and Armstrong, A.W. Nonmelanoma skin cancer. Dermatol. Clin. 2012, 30(1): 125-139.
Rivers, J.K. el al. Topical treatment of actinic keratoses with 3.0% diclofenac in 2.5% hyaluronan gel. Br J Dermatol. 2002, 146(1): 94-100.
Seckin, D. et. al. Can topical calcipotriol be a treatment alternative in actinic keratoses? A preliminary report. J Drugs Dermatol. 2009, 8(5): 451-4.
Pommergaard Hans-Christian et al: "Topical combination of diclofenac, calcipotriol, and difluoromethylornithine has beneficial effects comparable to 5-fluorouracil for the treatment of non-melanoma skin cancer in mice.", Journal of Chemotherapy Apr. 2014, vol. 26, No. 2, Apr. 2014 (Apr. 2014), pp. 105-110.
Horn Y et al: "Urinary polyamine levels in cancer patients treated with D,L-alpha-difluoromethylornithine, an inhibitor of polyamine biosynthesis.", Journal of Surgical Oncology Jul. 1989, vol. 41, No. 3, Jul. 1989 (Jul. 1989), pp. 177-182.
Danilenko Michael et al: "Enhancement by other compounds of the anti-cancer activity of vitamin D3 and its analogs", Experimental Cell Research, Elsevier, Amsterdam, NL, vol. 298, No. 2, Aug. 15, 2004, pp. 339-358.
Haider K Bangash et al: "Management of Non-Melanoma Skin Cancer in Immunocompromised Solid Organ Transplant Recipients", Current Treatment Options in Oncology, Current Science, Philadelphia, PA, US, vol. 13, No. 3, May 17, 2012, pp. 359-361.
Ferrer Guillen Blanca et al: "Improved effect on 2 cases of disseminated superficial actinic porokeratosis with daylight photodynamic therapy", Photodiagnosis and Photodynamic Therapy, Elsevier, Amsterdam, NL, vol. 23, Aug. 1, 2018, pp. 365-366.
Transmittal; International Search Report; and Written Opinion of the International Searching Authority for International Application No. PCT/US2018/059671 dated Feb. 20, 2019.

*Primary Examiner* — James D. Anderson
(74) *Attorney, Agent, or Firm* — Katten Munchin Rosenman LLP

(57) ABSTRACT

Topical compositions for dermal use comprising a TSLP inducing agent, a cytotoxic agent, and an NSAID agent and methods of using them for the treatment of precancerous and cancerous skin lesions are disclosed.

15 Claims, 57 Drawing Sheets

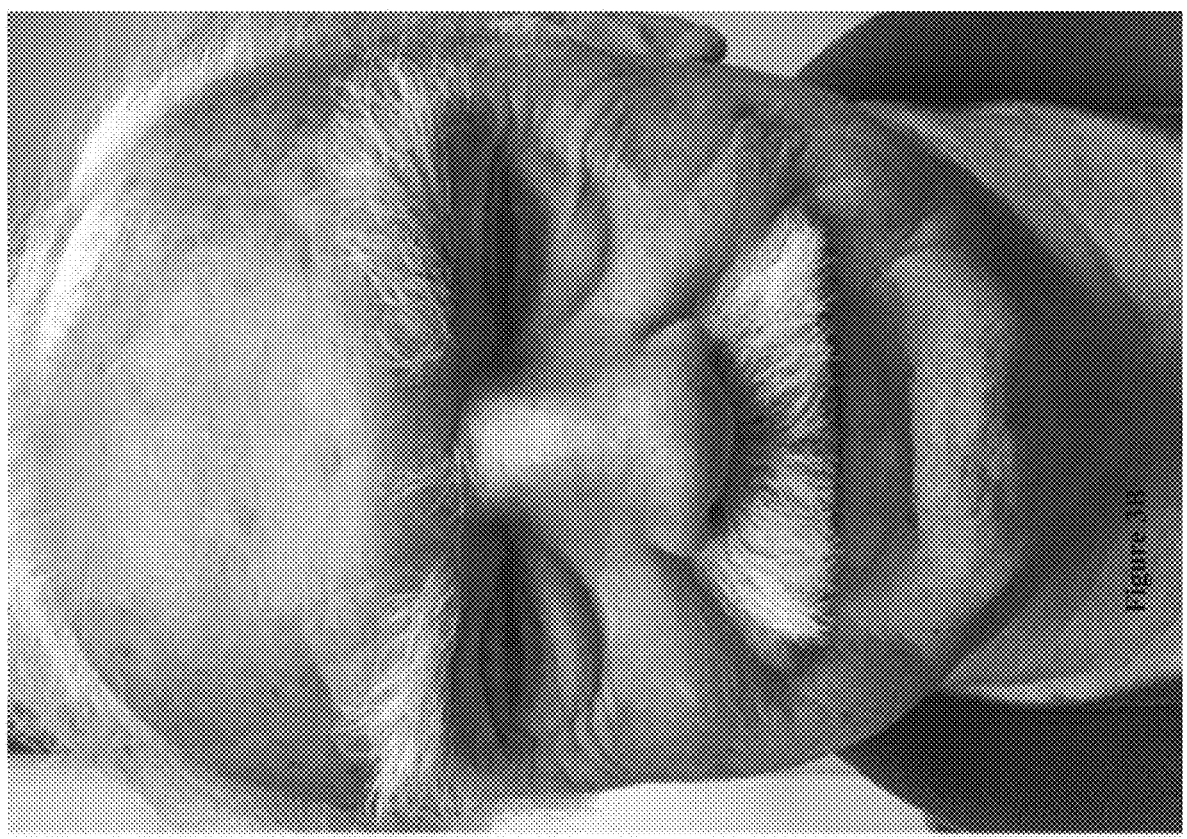

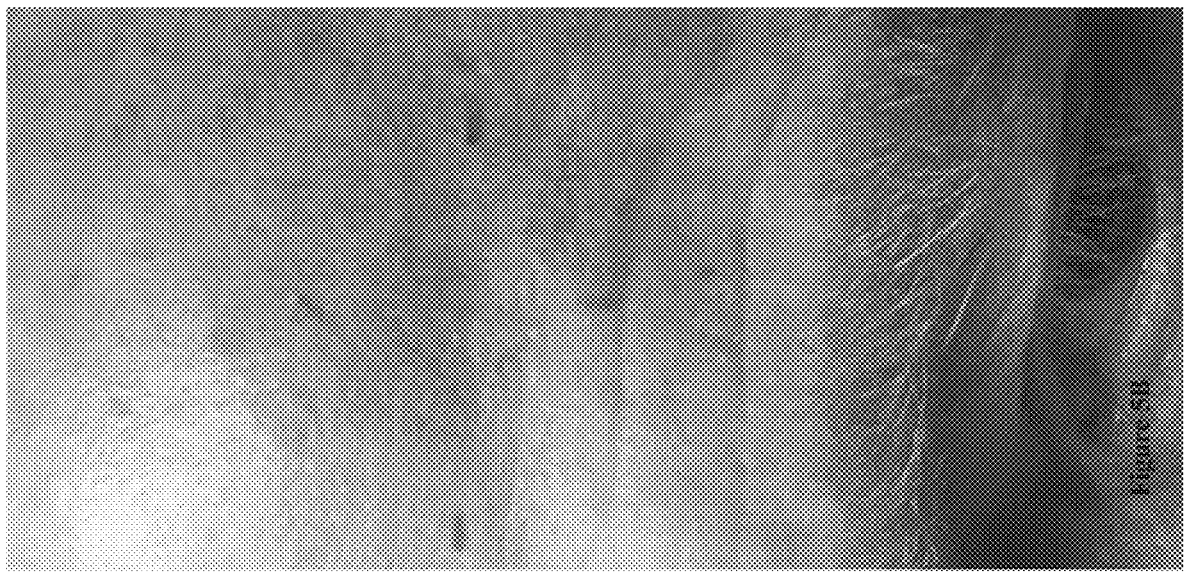

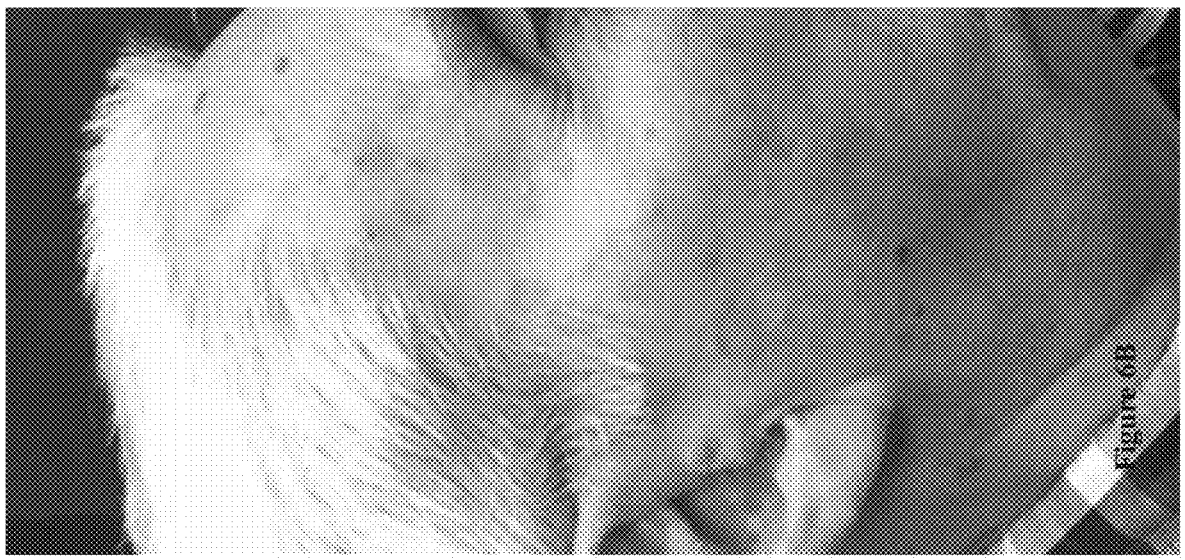

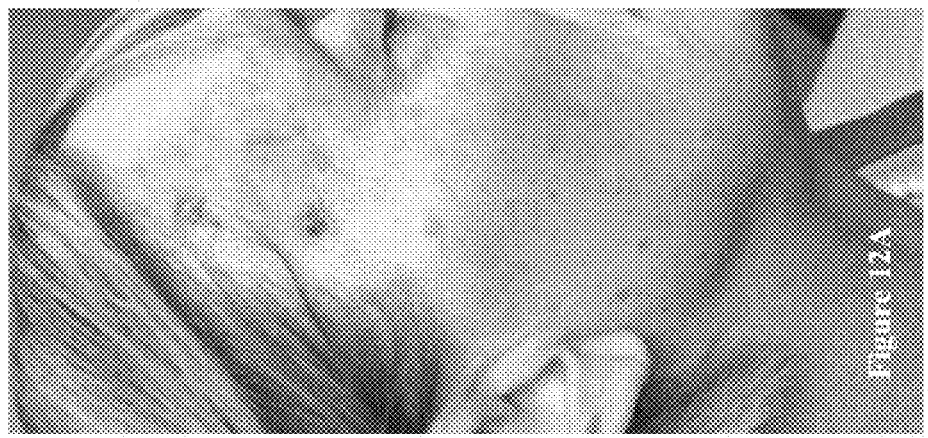

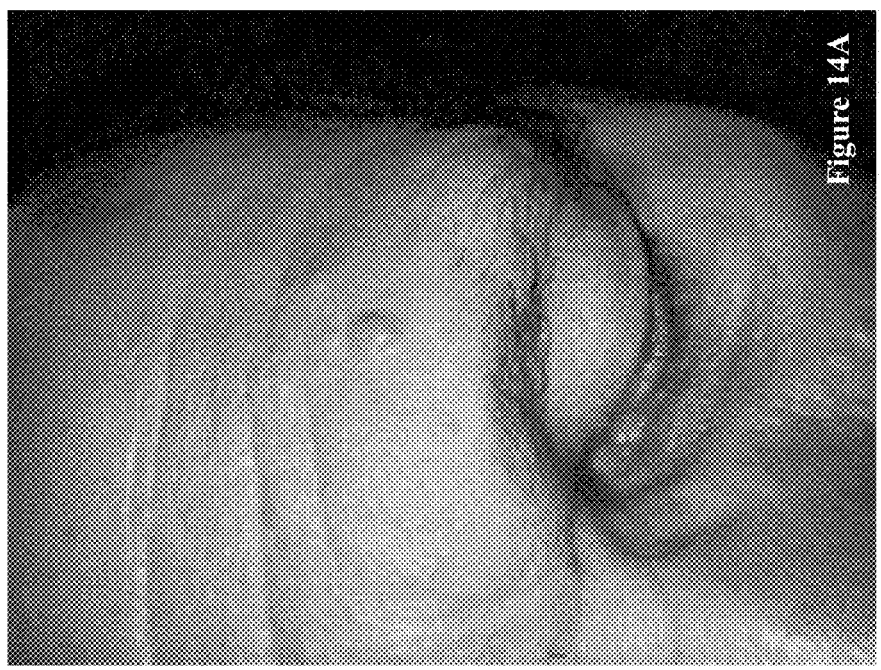

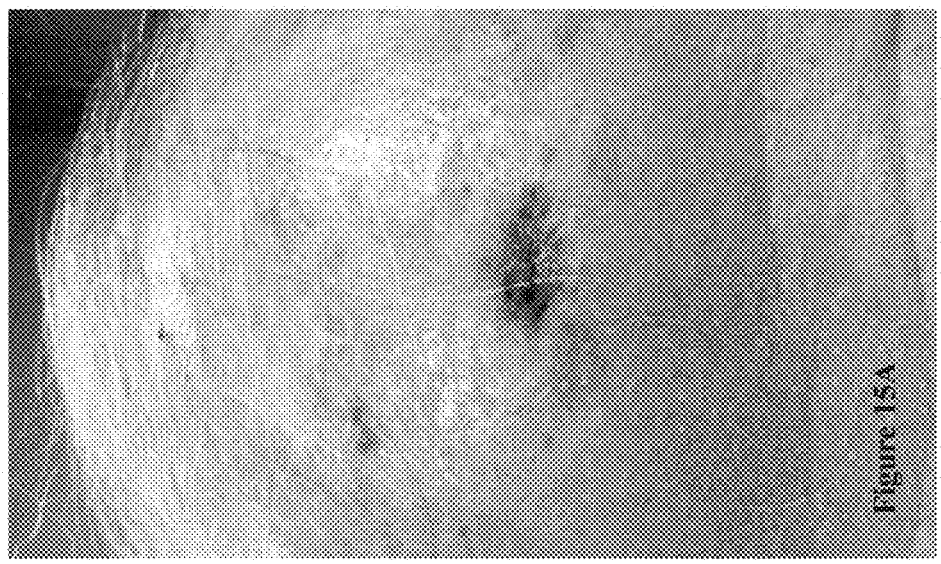

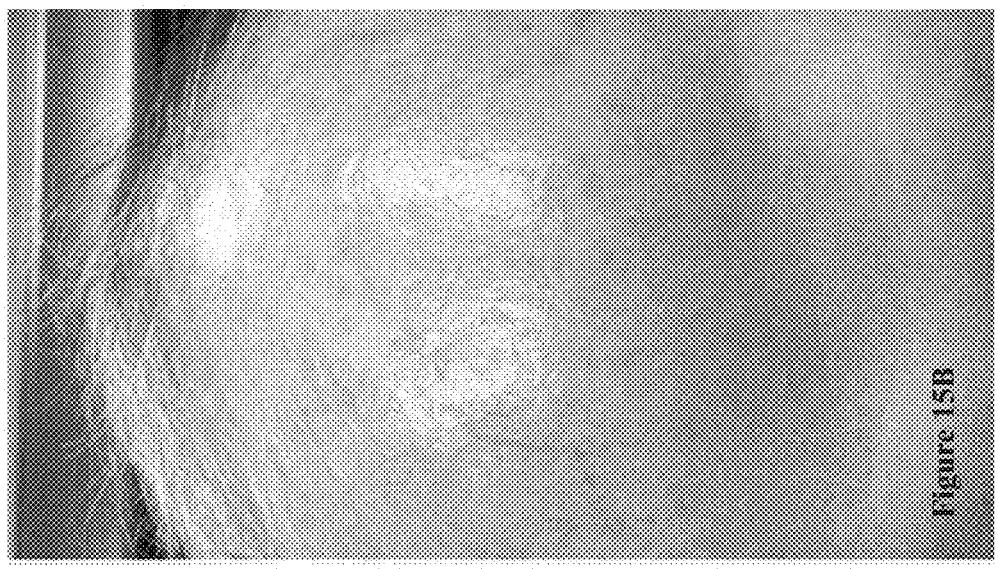

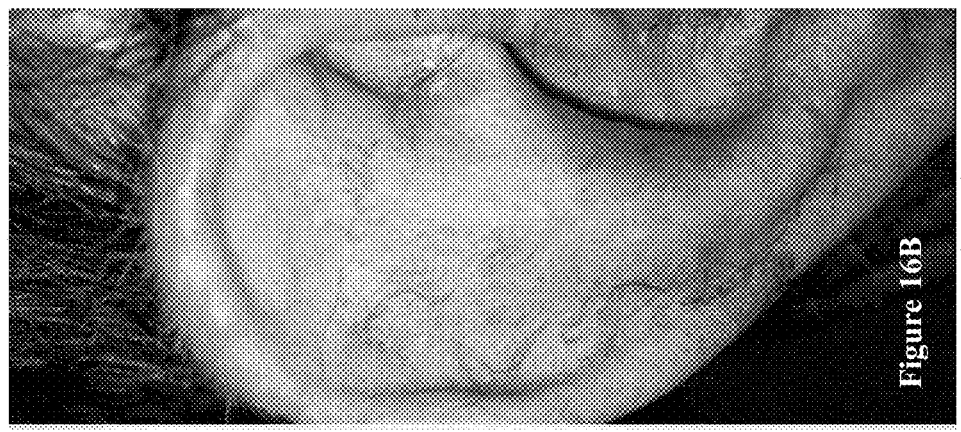

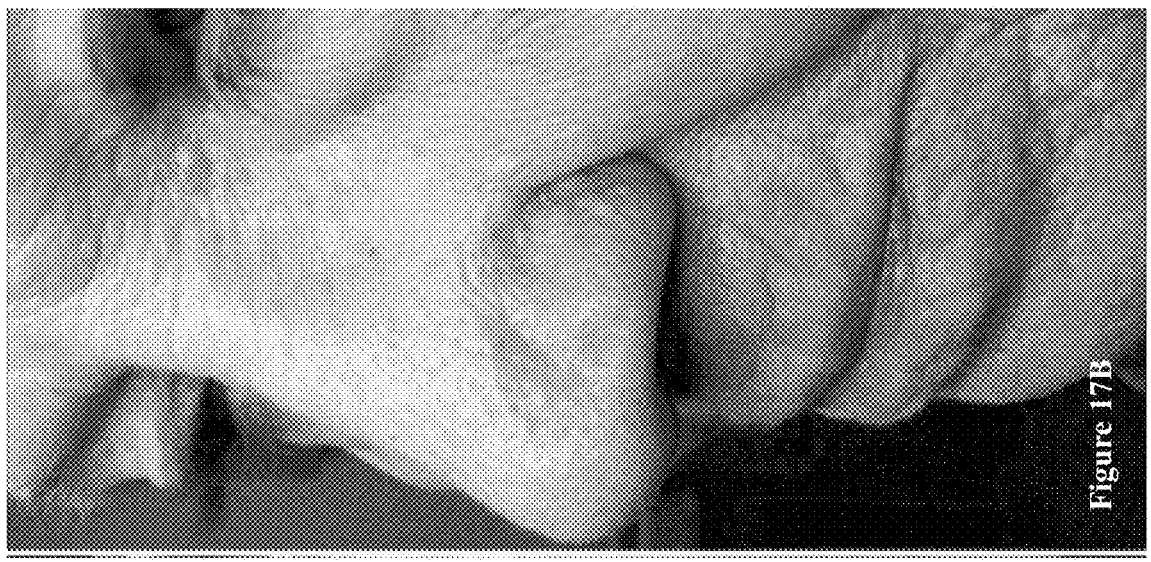

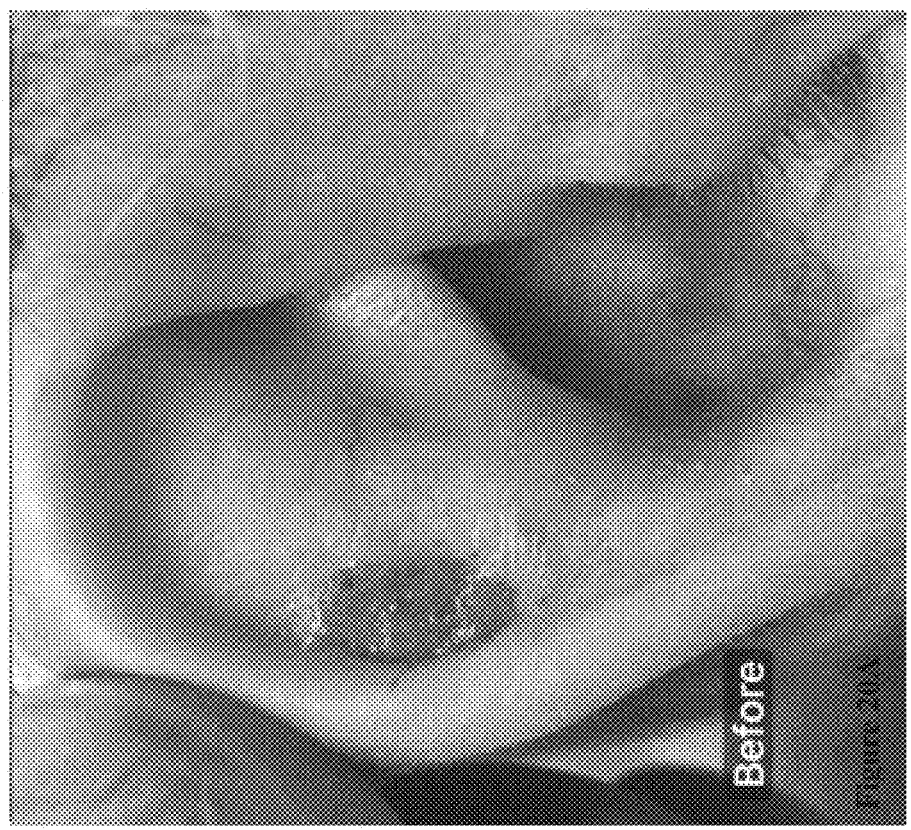

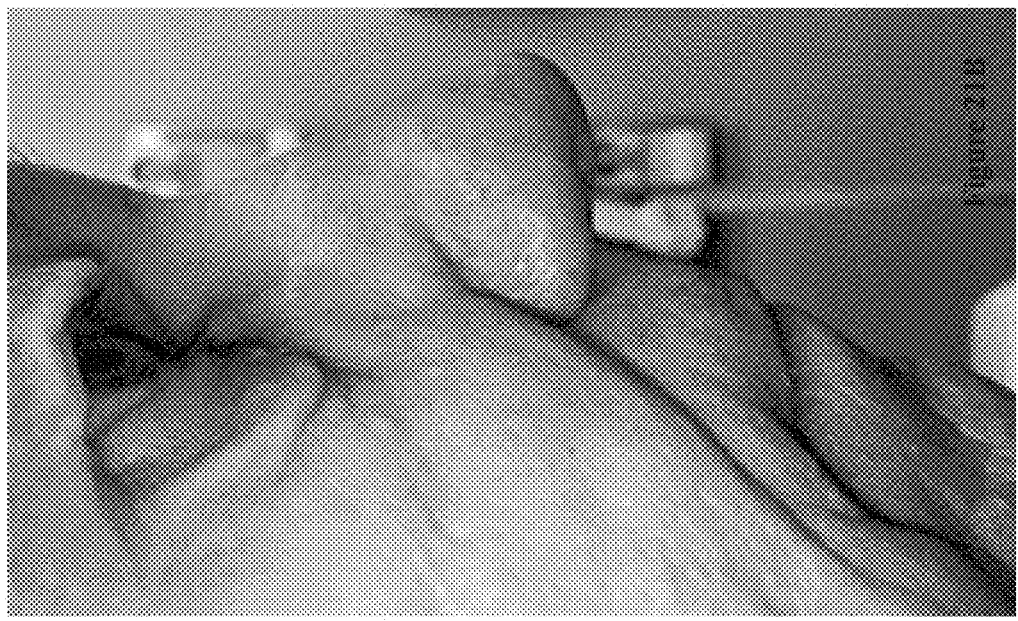

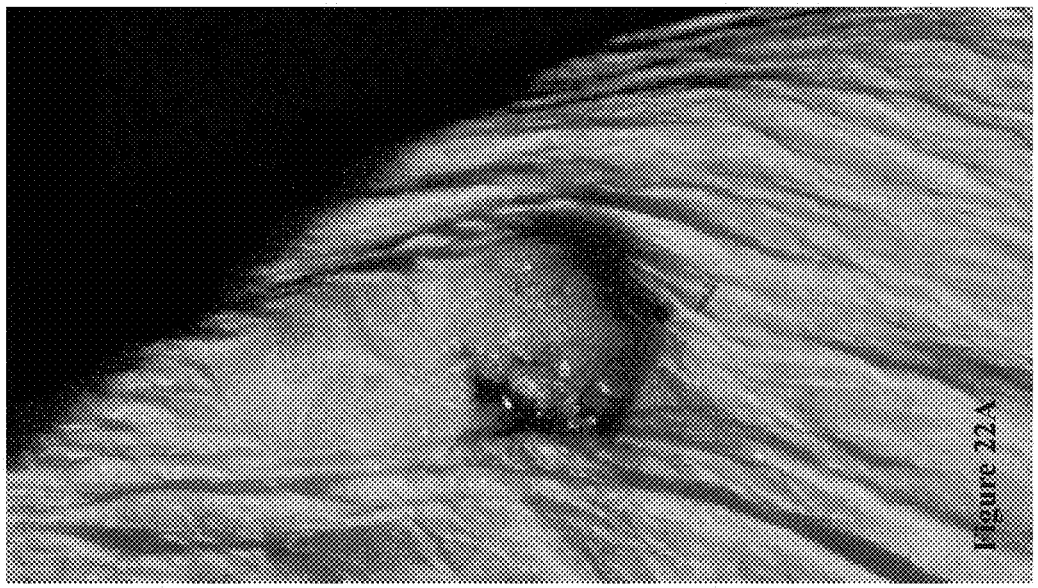

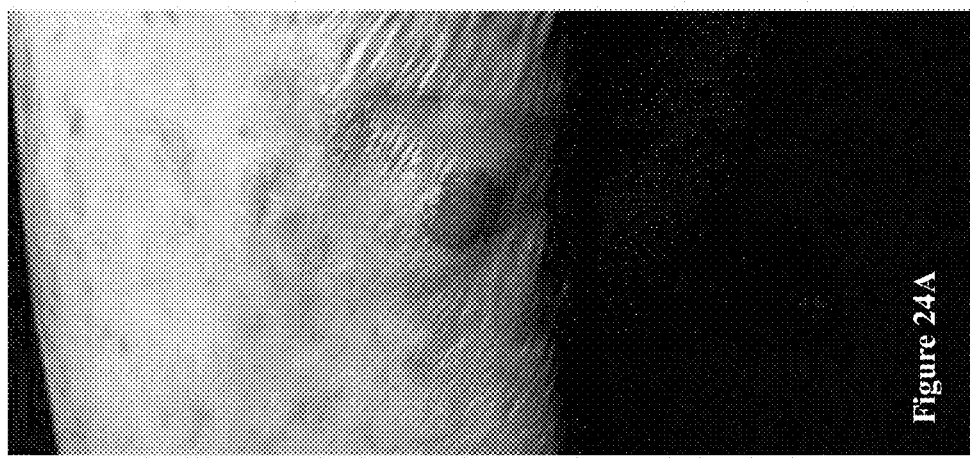

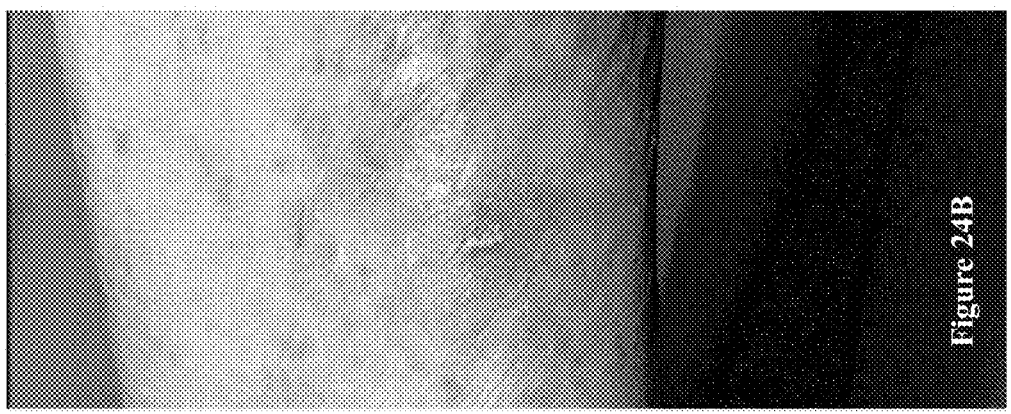

COMPOSITIONS AND METHODS FOR THE TREATMENT OF SKIN LESIONS

CROSS REFERENCE

This application claims the benefit under 35 U.S.C. § 119(e) of U.S. Provisional Patent Application No. 62/583,979, filed Nov. 9, 2017, which is herein incorporated by reference in its entirety.

BACKGROUND OF THE INVENTION

1. Technical Field

The present invention concerns pharmaceutical compositions for dermal use and methods of treating skin conditions with such compositions. More specifically, embodiments of the present invention can be used for the treatment of precancerous and cancerous skin lesions. Pharmaceutical compositions and methods of treatment of the invention comprise a thymic stromal lymphopoietin ("TSLP") inducing agent, a cytotoxic agent, and a non-steroidal anti-inflammatory ("NSAID") agent. Exemplary embodiments of the invention include pharmaceutical compositions containing calcipotriene, 5-fluorouracil ("5-FU"), and diclofenac. Certain embodiments of the present invention include methods of topically treating precancerous and cancerous skin lesions in human patients. More specifically, certain methods of the present invention involve topically administering a composition comprising a combination of calcipotriene, 5-FU, and diclofenac to humans suffering from actinic keratosis, basal cell carcinoma, and/or squamous cell carcinoma. Dramatic and unexpected results were observed in humans suffering from precancerous and cancerous skin lesions.

2. Background Art

Skin cancer is one of the most predominant forms of cancer. Basal cell carcinoma (a.k.a. basal cell cancer or BCC) and squamous cell carcinoma (a.k.a. squamous cell cancer or SCC) are two types of skin cancer that are known as non-melanoma skin cancer. Non-melanoma skin cancer is the most common type of skin cancer, accounting for more than 2 million new cases per year in the U.S. See, e.g., Kim, R. H. and Armstrong, A. W. Nonmelanoma skin cancer. Dermatol. Clin. 2012, 30(1): 125-139. BCC and SCC may be either superficial (limited to the epidermis) or penetrating to the dermis.

There are many precancerous stages and early stages of non-melanoma skin cancer. A precancerous skin lesion is a skin lesion that may potentially develop into skin cancer, but is not yet cancerous. A common precancerous skin lesion is actinic keratosis ("AK"). AK is caused by long-term exposure to sunlight and can lead to the development of SCC, if left alone.

One example of SCC is squamous cell carcinoma in situ, also known as Bowen's disease. It is an early stage of SCC. It occurs in male and female patients generally over 60 years. SCC in situ is often caused by chronic sun exposure.

Treatment of non-melanoma skin cancer depends on a variety of factors including the age of the person, the location of the cancer, and the specific type of cancer. Treatment commonly involves surgical removal but may also involve non-surgical options, such as radiation therapy or topical treatments. The use of topical treatment is often limited to a precancerous skin lesion, such as AK.

Many of the current topical treatment regimens utilize a cytotoxic agent that inhibits the synthesis of DNA, thereby disrupting tumor growth. One such cytotoxic agent is 5-fluorouracil ("5-FU"). 5-FU acts principally as an inhibitor of thymidylate synthase ("TS"), an enzyme involved in the synthesis of pyrimidine thymidine, which is a nucleoside required for DNA replication. Imiquimod is another commonly used topical non-steroidal treatment, which causes activation of the immune system. Topical treatment with diclofenac and calcipotriol have been reported for the treatment for AK. See, e.g., Rivers, J. K. et. al. Topical treatment of actinic keratoses with 3.0% diclofenac in 2.5% hyaluronan gel. Br J Dermatol. 2002, 146(1): 94-100; Seckin, D. et. al. Can topical calcipotriol be a treatment alternative in actinic keratoses? A preliminary report. J Drugs Dermatol. 2009, 8(5): 451-4.

Although some topical treatments exist, the long treatment duration and severe side effects have limited the efficacy of current topical AK, SCC, and BCC treatments. Therefore, there is still a need in this field for improved anti-skin cell carcinoma pharmaceuticals that are either faster acting or have less side effects. Inclusion of NSAIDs in a topical formulation offer the possibility of achieving local therapeutic benefit while eliminating or reducing side effects.

SUMMARY OF THE INVENTION

The present invention concerns a composition for dermal use. According to a first embodiment, the present invention is directed to a topical composition comprising a first component comprising at least one TLSP-inducing agent, a second component comprising at least one cytotoxic agent, a third component comprising at least one NSAID, and one or more excipients. In some embodiments, the first component comprises vitamin D or a vitamin D analogue, or a pharmaceutically acceptable salt, polymorph, or solvate thereof. In a preferred embodiment, the first component comprises calcipotriene or a pharmaceutically acceptable salt, polymorph, or solvate thereof. In some embodiments, the second component comprises 5-fluorouracil or a pharmaceutically acceptable salt, polymorph, or solvate thereof. In some embodiments, the third component comprises diclofenac or a pharmaceutically acceptable salt, polymorph, or solvate thereof. In some embodiments, the first component comprises about 0.002% to about 0.005% of the composition.

In some embodiments, the second component comprises about 1% to about 5% of the composition. In some embodiments, the third component comprises about 1% to about 5% of the composition.

According to a second embodiment, the present invention is directed to a topical composition comprising about 1% to about 2.5% 5-fluorouracil; about 0.005% calcipotriene; about 3% diclofenac sodium; and one or more excipients.

More specifically, embodiments of the present invention include topical compositions for treating precancerous or cancerous skin lesions, such as AK, BCC, and SCC. SCC includes, but is not limited to, SCC in situ (Bowen's disease). BCC and SCC also include, but are not limited to, superficial BCC and SCC. In a preferred embodiment, the topical composition comprises a vitamin D or vitamin D analogue, 5-fluorouracil, and diclofenac sodium for the treatment of precancerous and cancerous skin lesions. In a more preferred embodiment, the topical pharmaceutical composition comprises calcipotriene, 5-fluorouracil, and diclofenac for the treatment of precancerous and cancerous skin lesions such as AK, BCC, and SCC. In a most preferred embodiment, the topical pharmaceutical composition comprises about 0.005% calcipotriene, about 1% to about 2.5% 5-fluorouracil, and about 3% diclofenac sodium for the treatment of precancerous and cancerous skin lesions such as AK, BCC, and SCC.

BRIEF DESCRIPTION OF THE DRAWINGS

FIG. 3A is a picture of a patient with a SCC in situ lesion on a face before treatment according to specific embodiments of the present invention.

FIG. 3B is a picture of a patient with a SCC in situ lesion on a face after treatment according to specific embodiments of the present invention.

FIG. 4A is a picture of a patient with a nodular BCC lesion before treatment according to specific embodiments of the present invention.

FIG. 4B is a picture of a patient with a nodular BCC lesion after treatment according to specific embodiments of the present invention.

FIG. 5B is a picture of a patient with a SCC lesion on a face after treatment according to specific embodiments of the present invention.

FIG. 6A is a picture of a patient with a SCC in situ lesion on a face before treatment according to specific embodiments of the present invention.

FIG. 6B is a picture of a patient with a SCC in situ lesion on a face after treatment according to specific embodiments of the present invention.

FIG. 8A is a picture of a patient with a SCC in situ lesion on a face before treatment according to specific embodiments of the present invention.

FIG. 8B is a picture of a patient with a SCC in situ lesion on a face during treatment according to specific embodiments of the present invention.

FIG. 8C is a picture of a patient with a SCC in situ lesion on a face after treatment according to specific embodiments of the present invention.

FIG. 9A is a picture of a patient with a BCC lesion before treatment according to specific embodiments of the present invention.

FIG. 9B is a picture of a patient with a BCC lesion before treatment according to specific embodiments of the present invention.

FIG. 9D is a picture of a patient with a BCC lesion after treatment according to specific embodiments of the present invention.

FIG. 10C is a picture of a patient with a SCC in situ lesion after treatment according to specific embodiments of the present invention.

FIG. 11A is a picture of a patient with a BCC lesion before treatment according to specific embodiments of the present invention.

FIG. 11B is a picture of a patient with a BCC lesion after treatment according to specific embodiments of the present invention.

FIG. 12A is a picture of a patient with a BCC lesion before treatment according to specific embodiments of the present invention.

FIG. 13A is a picture of a patient with a SCC lesion on a shin before treatment according to specific embodiments of the present invention.

FIG. 14A is a picture of a patient with a BCC lesion before treatment according to specific embodiments of the present invention.

FIG. 15A is a picture of a patient with a SCC lesion before treatment according to specific embodiments of the present invention.

FIG. 15B is a picture of a patient with a SCC lesion after treatment according to specific embodiments of the present invention.

FIG. 16A is a picture of a patient with a SCC lesion before treatment according to specific embodiments of the present invention.

FIG. 16B is a picture of a patient with a SCC lesion after treatment according to specific embodiments of the present invention.

FIG. 17A is a picture of a patient with a BCC lesion before treatment according to specific embodiments of the present invention.

FIG. 17B is a picture of a patient with a BCC lesion after treatment according to specific embodiments of the present invention.

FIG. 18B is a picture of a patient with a BCC lesion on an arm after treatment according to specific embodiments of the present invention.

FIG. 19B is a picture of a patient with a BCC lesion after treatment according to specific embodiments of the present invention.

FIG. 20A is a picture of a patient with a BCC lesion before treatment according to specific embodiments of the present invention.

FIG. 21A is a picture of a patient with a BCC lesion before treatment according to specific embodiments of the present invention.

FIG. 21B is a picture of a patient with a BCC lesion after treatment according to specific embodiments of the present invention.

FIG. 22A is a picture of a patient with a SCC lesion on an arm before treatment according to specific embodiments of the present invention.

FIG. 23A is a picture of a patient with a SCC lesion on a shin before treatment according to specific embodiments of the present invention.

FIG. 23B is a picture of a patient with a SCC lesion on a shin after treatment according to specific embodiments of the present invention.

FIG. 24A is a picture of a patient with a SCC lesion on a calf before treatment according to specific embodiments of the present invention.

FIG. 24B is a picture of a patient with a SCC lesion on a calf after treatment according to specific embodiments of the present invention.

FIG. 25A is a picture of a patient with a BCC lesion before treatment according to specific embodiments of the present invention.

FIG. 25B is a picture of a patient with a BCC lesion after treatment according to specific embodiments of the present invention.

DETAILED DESCRIPTION OF THE PRESENTLY PREFERRED EXEMPLARY EMBODIMENTS

Figure 1A:
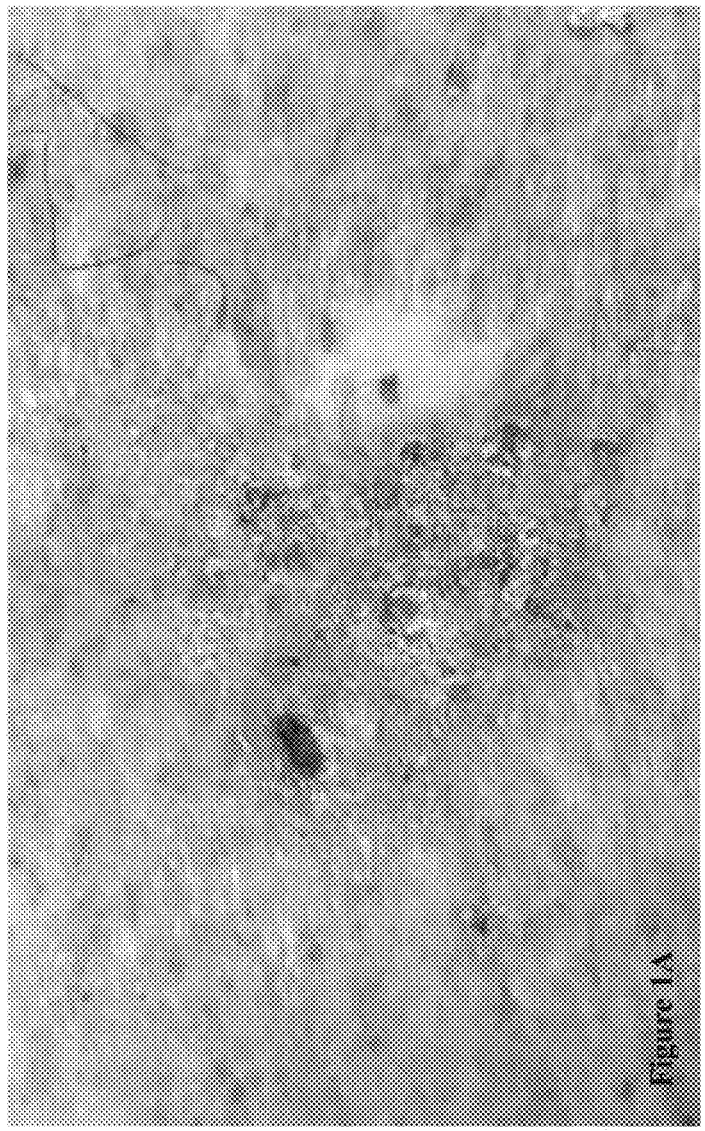
FIG. 1A is a picture of a patient with a nodular BCC lesion before treatment according to specific embodiments of the present invention.

Preferred embodiments of the present invention will be described herein below. In the following description, well-known formulations or methods are not described in detail since they would obscure the invention in unnecessary detail.

Unless indicated otherwise, all ingredient amounts presented as a percentage are in units of weight %. The active ingredients in these compositions may be provided in the form of an acceptable salt, polymorph, or solvate. The active ingredients in these compositions may also be provided in the form of acceptable prodrugs.

In a first embodiment, a composition comprises a first component comprising at least one TSLP-inducing agent, a second component comprising at least one cytotoxic agent, a third component comprising at least one NSAID agent, and one or more excipients. In some embodiments, a composition comprises a first component that is capable of inducing thymic stromal lymphopoietin (TSLP), i.e. a TSLP-inducing agent. Preferred TSLP-inducing agents may include vitamin D or a vitamin D analogue. Especially preferred TSLP-inducing agents are compounds selected from the group consisting of seocalcitol; calcipotriene; calcitriol; tacalcitol, maxacalcitol; paricalcitol; falecalcitriol; $1\alpha, 24S$-dihydroxy-vitamin D2; and 1(S),3(R)-dihydroxy-20(R)-[((3-(2-hydroxy-2-propyl)-phenyl)-methoxy)-methyl]-9,10-seco-pregna-5(Z),7(E),10(19)-triene, their salts or pro-drugs, as well as mixtures thereof. Even more preferred TSLP-inducing agents are vitamin D analogues selected from the group consisting of calcipotriene, calcitriol, tacalcitol, maxacalcitol, and 1(S),3(R)-dihydroxy-20(R)-[((3(2-hydroxy-2-propyl)-phenyl)-methoxy)-methyl]-9,10-seco-pregna-5(Z),7(E), 10(19)-triene as well as mixtures thereof.

In some embodiments, synthetic vitamin D analogues are more preferred over naturally occurring vitamin D or vitamin D analogues as the therapeutic effects of the latter may be less selective for the treatment of skin diseases, such as skin lesions. In a preferred embodiment, a vitamin D analogue is calcipotriene, a synthetic derivative of calcitriol. Calcipotriene, and other TSLP-inducing agents, are commercially available from sources such as Medisca®.

Dosages of a TSLP-inducing agent can vary depending upon the disease or disorder to be treated and/or the age and condition of the subject to be treated. In some embodiments of the invention the first component comprises about 0.001% to about 20%, from about 0.001% to about 10%, from about 0.001% to about 1%, from about 0.001% to about 0.1% or, more preferably, from about 0.001% to about 0.01% of the composition. In a specific embodiment, a TSLP-inducing agent is a vitamin D analogue. Dosages of a vitamin D analog can vary depending upon the disease or disorder to be treated and/or the age and condition of the subject to be treated. In certain embodiments, the concentration of vitamin D analog in the composition may be from about 0.001% to about 0.1% or, more preferably, from about 0.001% to about 0.01%. In a preferred embodiment, a vitamin D analogue is calcipotriene wherein the concentration of calcipotriene in the composition is preferably about 0.005%.

In some embodiments, a composition comprises a second component that is a cytotoxic agent. The cytotoxic agent may be an alkylating agent, an antimetabolite, an anti-tumor antibiotic, an anticytoskeletal agent, a topoisomerase inhibitor, an anti-hormonal agent, a targeted therapeutic agent, an angiogenesis inhibitor, a growth inhibitory polypeptide, a photodynamic therapeutic agent, an antineoplastic agent, or a combination thereof. In a specific embodiment, a cytotoxic agent is an antimetabolite. Suitable antimetabolites may include, but are not limited to, aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate. In a preferred embodiment, an antimetabolite is 5-FU. 5FU, and other cytotoxic agents, are commercially available from sources such as Medisca®.

Dosages of a cytotoxic agent can vary depending upon the disease or disorder to be treated and/or the age and condition of the subject to be treated. For example, the concentration of cytotoxic agent in certain embodiments of the invention may be from about 0.01% to about 25%, or about 0.1% to about 10% or, more preferably, from about 0.5% to about 5%. In a specific embodiment, the concentration of cytotoxic agent in the composition is about 2.5%. In another preferred embodiment, the concentration of cytotoxic agent in the composition is about 5%. In a specific embodiment, a cytotoxic agent is 5-FU wherein the concentration of 5-FU in the composition may be from about 0.1% to about 10% or, more preferably, from about 0.5% to about 5%. In a preferred embodiment, the concentration of 5-FU in the composition is about 2.5%. In another preferred embodiment, the concentration of 5-FU in the composition is about 1%.

In some embodiments, a composition comprises a third component, which is preferably a nonsteroidal anti-inflammatory drug (NSAID). Suitable NSAIDs may include, but are not limited to, aspirin, ibuprofen, naproxene, indomethacin, fenoprofen, flurbiprofen, and diclofenac. In a preferred embodiment, the NSAID is diclofenac sodium. Diclofenac sodium, and other NSAIDs are commercially available from sources such as Medisca®.

Dosages of the topical NSAID can vary depending upon the disease or disorder to be treated as well as the age and condition of the subject to be treated. For example, the concentration of NSAID in certain embodiments of the invention may be from about 0.1% to about 10%, or about 1% to about 5%. In a specific embodiment, the NSAID is diclofenac wherein the concentration of diclofenac in the composition preferably may be from about 0.1% to about 10% or, more preferably, from about 1% to about 5%. In an especially preferred embodiment, the concentration of diclofenac is about 3%.

Another embodiment comprises compositions for topical administration, which may be formulated as an ointment, a cream, a lotion, a scalp lotion, a suspension, a powder, a solution, a paste, a spray, am aerosol, an oil, an oil in water emulsion, a liniment or other spreadable liquid or semi liquid preparation. Topical administration may also involve the use of transdermal administration such as transdermal patches or iontophoresis devices. The pharmaceutical compositions for use in accordance with the present invention can be formulated in any conventional manner using one or more pharmaceutically acceptable excipients or carriers. A pharmaceutically acceptable excipient or carrier, as used herein, the term "pharmaceutically acceptable" means approved by a regulatory agency of the Federal or a State Government or listed in the U.S. Pharmacopoeia or other generally recognized pharmacopoeia for use in mammals, and more particularly in humans.

In a further preferred embodiment the invention provides a composition for dermal use, said composition comprising:
  a first component consisting of at least one TSLP-inducing agent;
  a second component consisting of at least one cytotoxic agent;
  a third component consisting of at least one NSAID; and
  one or more pharmaceutically acceptable excipient or carrier.

An especially preferred embodiment of the invention is an oil in water emulsion for dermal use comprising:
  Calcipotriene (about 0.005%)
  5-Fluorouracil (about 1 or about 2.5%)
  Diclofenac sodium (about 3%)
  Isopropyl Myristate (about 12 to about 17%)
  Cetyl Alcohol (about 1 to about 3%)
  Cetearyl Alcohol (about 1 to about 3%)
  Polysorbate 60 (about 1 to about 4%)
  Glyceryl Stearate (about 1 to about 4%)
  PEG 100 Stearate (about 1 to about 4%)
  Propylene Glycol (about 8 to about 12%)
  Hydroxymethyl Aminomethane (about 2 to about 4%)
  Hydroxymethyl Aminomethane HCL (about 1 to about 2%)
  Benzyl Alcohol (about 1 to about 3%)
  Purified water The applicant has unexpectedly found that topical administration of pharmaceutical compositions comprising a TSLP-inducing agent, a cytotoxic agent, and a NSAID is effective in the treatment of precancerous and cancerous skin lesions. In certain embodiments, a therapeutically active amount of one or more compositions comprising a TSLP-inducing agent, a cytotoxic agent, and an NSAID may be administered to a human diagnosed as having AK, BCC, or SCC. Administration is performed using standard techniques known in the art. In a preferred embodiment, the composition is administered topically. Pharmaceutical compositions may be administered topically as an ointment, a cream, a lotion, a scalp lotion, a suspension, a powder, a solution, a paste, a spray, am aerosol, an oil, an oil in water emulsion, a liniment or other spreadable liquid or semi-liquid preparation. Topical administration may also involve the use of transdermal administration such as transdermal patches or iontophoresis devices. In preferred embodiments, a composition of the invention is administered to a person as a topical ointment or cream. In a more preferred embodiment, a composition of the invention is administered to a person as an oil in water emulsion.

The methods of the present invention involve diagnosing a person as having AK, BCC, or SCC. Once diagnosed with AK, BCC, or SCC, a preferred method of the present invention involves topically administering to the affected skin of a person in need of such treatment one or more compositions comprising one or more TSLP-inducing agents, one or more cytotoxic agents, and one or more NSAIDs. The methods preferably include the step of topically administering the composition(s) once or twice daily of an effective amount of said composition(s) on the affected area of the skin for 7 to 14 days. In certain embodiments, such treatments are effective in treating, reducing, or curing lesions within 14 days of daily administration.

In certain aspects of the invention, the precancerous skin lesion is AK. Methods of identifying AK are known in the art, such as physical exam, or skin biopsy. In a specific embodiment of the invention, the topical administration of composition(s) comprising calcipotriene, 5-FU, and diclofenac is effective to treat, reduce, or cure AK. Said method preferably comprises topical administration once or twice daily of a dosage effective amount of said composition. In certain embodiments, such treatments are effective in treating, reducing, or curing AK within 14 days of daily administration.

In another embodiment, the methods of the invention can be used to treat BCC, SCC or SCC in situ (Bowen's disease). Methods of identifying BCC, SCC or SCC in situ are known in the art, such as physical exam, or a skin biopsy. In a specific embodiment of the invention, the topical administration of composition(s) comprising calcipotriene, 5-FU, and diclofenac is effective to treat BCC, SCC or SCC in situ. The method preferably comprises topical administration once or twice daily of a medically sufficient dosage of said composition. In certain embodiments, such treatments are effective in treating, reducing, or curing BCC, SCC or SCC in situ within 14 days of daily administration.

Effective amounts of compositions of the present invention will generally depend on a variety of factors including, but not limited to, the number of lesions, the size of the lesions, and the location of the lesions. Typically, an effective amount of the composition is about 0.1 to about 100 mg. In a preferred embodiment comprising a TSLP inducing agent, a cytotoxic compound and a NSAID, the effective amount is typically about 1 to 50 mg. In a more preferred embodiment comprising calcipotriene, 5-FU, and diclofenac, the effective amount is preferably about 5 to about 30 mg.

Until now a topical pharmaceutical composition comprising a combination of a TSLP-inducing agent, a cytotoxic agent, and an NSAID for the treatment of precancerous and cancerous skin lesions has not been described. Surprisingly, investigations described herein have shown that the topical administration of a composition comprising these three components (and especially when calcipotriene, 5-FU, and diclofenac) is dramatically effective in the treatment of AK, BCC, SCC, and SCC in situ. The present invention also relates to methods of treating precancerous and cancerous skin lesions using the compositions described above, as well as novel topical formulations. The invention is further illustrated by the following, non-limiting examples.

Example 1: Representative Formulations

Topical cream containing calcipotriene, 5-FU, and diclofenac. Table 1 shows preferred formulations according to the invention.

| Ingredients | A (wt. %) | B (wt. %) |
|---|---|---|
| Calcipotriene | 0.005 | 0.005 |
| 5-FU | 1 | 2.5 |
| Diclofenac sodium | 3 | 3 |
| Isopropyl Myristate | about 12 to about 17 | about 12 to about 17 |
| Cetyl Alcohol | about 1 to about 3 | about 1 to about 3 |

-continued

| Ingredients | A (wt. %) | B (wt. %) |
|---|---|---|
| Cetearyl Alcohol | about 1 to about 3 | about 1 to about 3 |
| Polysorbate 60 | about 1 to about 4 | about 1 to about 4 |
| Glyceryl Stearate | about 1 to about 4 | about 1 to about 4 |
| PEG 100 Stearate | about 1 to about 4 | about 1 to about 4 |
| Propylene Glycol | about 8 to about 12 | about 8 to about 12 |
| Hydroxymethyl Aminomethane | about 2 to about 4 | about 2 to about 4 |
| Hydroxymethyl Aminomethane HCL | about 1 to about 2 | about 1 to about 2 |
| Benzyl Alcohol | about 1 to about 3 | about 1 to about 3 |
| Purified water | q. s. | q. s. |

Formulations A and B were made using the following method:
A) Heat Water to 75° C. Add Benzyl Alcohol and allow to dissolve.
B) Heat Isopropyl Myristate, Cetyl Alcohol, Polysorbate 60, Glyceryl Stearate, PEG 100 Stearate, and Cetearyl Alcohol to 75° C.
C) Add mixture from step (B) to solution from step (A) and keep mixing.
D) Heat propylene glycol to 75° C. and dissolve Hydroxymethyl Aminomethane and Hydroxymethyl Aminomethane HCL. Adjust pH to create a buffer system to maintain the target pH.
E) Add mixture (D) to mixture (C) with continued agitation.
F) Add 5-FU and Diclofenac to mixture (E).
G) Disperse Calcipotriene in a small amount of Propylene glycol and add to (F) at 50° C. Continue to mix while lowering temperature to 20-23° C.

Example 2: Study in Persons Diagnosed with AK, BCC, SCC and/or SCC In Situ

Formulations A and B were tested by the inventor, who is a licensed dermatologist. The study demonstrates the dramatic effect of the formulations according to the invention comprising calcipotriene, 5-FU, and diclofenac on precancerous and cancerous skin lesions. A summary of the study details for AK, superficial BCC, and superficial SCC in situ, is provided below.

| Summary of study | | |
|---|---|---|
| Study objectives | Investigate the clinical effect of Formulation A and B on patients suffering from actinic keratosis, superficial basal cell carcinoma and superficial squamous cell carcinoma in situ | |
| Patient population | A total of approximately 500 patients were treated at the inventor's dermatology center in Buffalo Grove, IL between February 2017 and November 2017 | |
| Inclusion Criteria | Clinical diagnosis of AK, BCC, and/or SCC in situ, gave informed consent, and agreed to follow inventor's treatment procedures | |
| Dose regimes | actinic keratosis of the scalp | Eligible patients are treated with Formulation B, applied on the affected area each night for 10 to 14 consecutive nights |
| | actinic keratosis of the face | Eligible patients are treated with Formulation B, applied on the affected area each night for 7 to 14 consecutive nights |
| | actinic keratosis of the chest | Eligible patients are treated with Formulation A, applied on the affected area each night for 7 consecutive nights |
| | superficial basal cell carcinoma | Formulation B used twice a day on the affected area for 7 to 14 consecutive nights |
| | basal cell carcinoma | Formulation B used twice a day on the affected area for 10 to 14 consecutive nights |

| Summary of study | | |
|---|---|---|
| | squamous cell carcinoma in situ | Formulation B used twice a day on the affected area for 7 to 14 consecutive nights |
| | squamous cell carcinoma | Formulation B used twice a day on the affected area for 10 to 14 consecutive nights |
| Evaluation | Patient self-assessment of pain and tenderness on a daily basis. Physician evaluation on day 7 of signs and symptoms of AK, (superficial) BCC, and (superficial) SCC (in situ), including signs of inflammation, irritation, tenderness, and discomfort. | |
| Overall conclusions | After treatment, an average reduction of approximately 95% and 90% was observed for AK on the face and scalp, respectively. An average reduction of approximately 95% was observed for AK on the chest. An average reduction of approximately 95% was observed for superficial BCC and SCC in situ. An average reduction of approximately 85% was observed for BCC and SCC. Patients reported a reduction of redness, irritation. Patients reported pain relief. | |

Table 2 shows the treatment regimens and treatment results of the tested formulations A and B.

TABLE 2

| | Treatment regimen | Average reduction of the respective lesion on the affected skin |
|---|---|---|
| actinic keratosis (face) | Formulation B used each night for seven to fourteen consecutive nights | 95% |
| actinic keratosis (scalp) | Formulation B used each night for ten to fourteen consecutive nights | 90% |
| actinic keratosis (chest) | Formulation A used each night for seven consecutive nights | 95% |
| superficial basal cell carcinoma | Formulation B used twice a day for seven to fourteen consecutive nights | 95% |
| basal cell carcinoma | Formulation B used twice a day for ten to fourteen consecutive nights | 85% |
| squamous cell carcinoma in situ | Formulation B used twice a day for seven to fourteen consecutive nights | 95% |
| squamous cell carcinoma | Formulation B used twice a day for ten to fourteen consecutive nights | 85% |

Results

The patient data obtained in this study demonstrated that embodiments of the invention comprising calcipotriene, 5-FU, and diclofenac had a dramatic reducing effect on the occurrence of AK on the face, the scalp and the chest and on BCC and SCC (in situ). These results are demonstrated by the exemplary pictures of individual patients below.

1
Lesion: BCC on patient's skin
Formulation: B, twice daily
Duration of treatment: 10 days

Figure 1B:
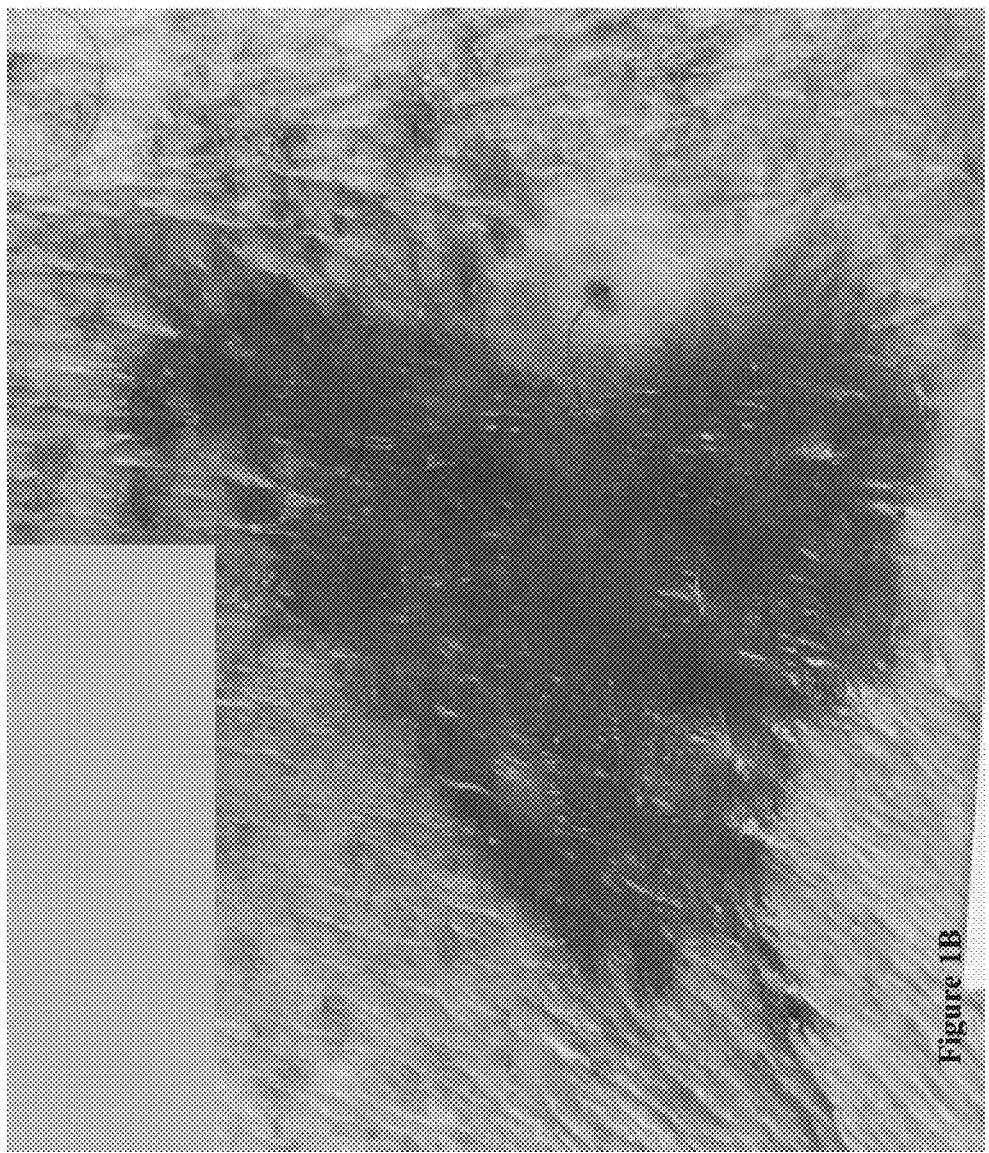
FIG. 1B is a picture of a patient with a nodular BCC lesion during treatment according to specific embodiments of the present invention.
Figure 1C:
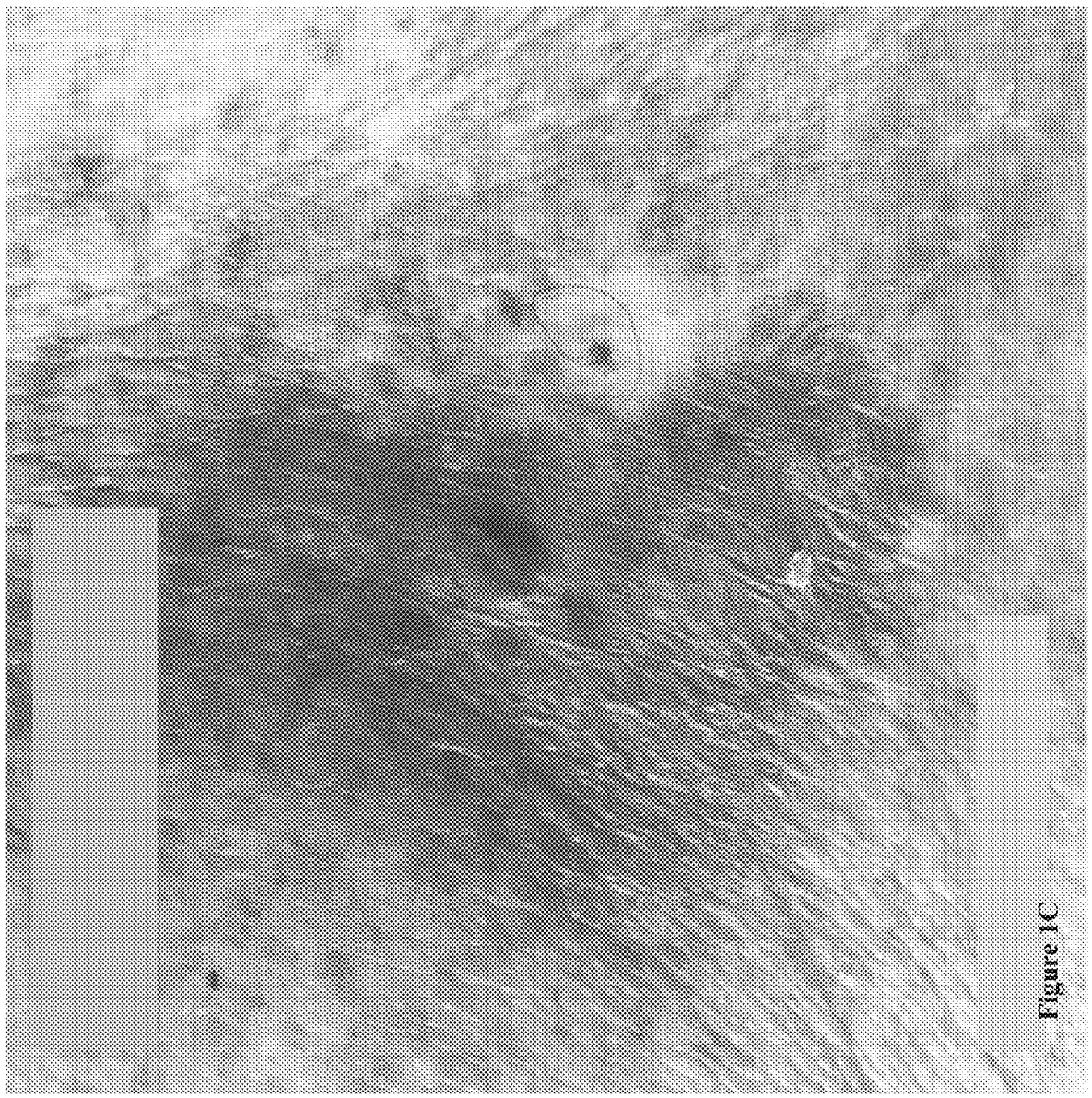
FIG. 1C is a picture of a patient with a nodular BCC lesion after treatment according to specific embodiments of the present invention.
Figure 1D:
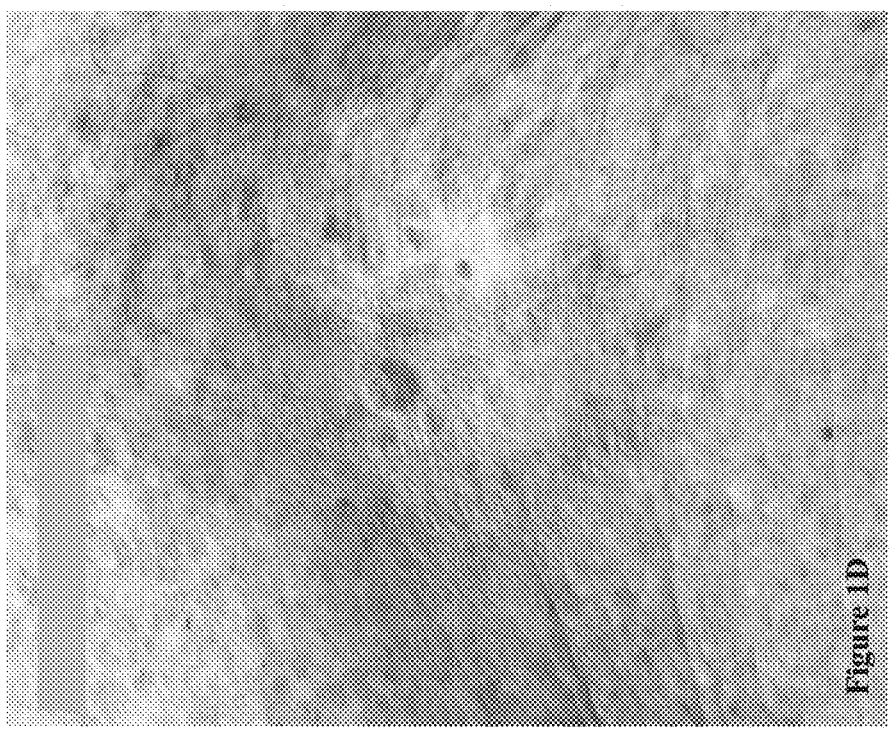
FIG. 1D is a picture of a patient with a nodular BCC lesion after treatment according to specific embodiments of the present invention.

| Before treatment | Day 10 of treatment | After treatment | After treatment |
|---|---|---|---|
| FIG. 1A | FIG. 1B | FIG. 1C | FIG. 1D |

2
Lesion: BCC on patient's skin
Formulation: B, twice daily
Duration of treatment: 10 days

Figure 2A:
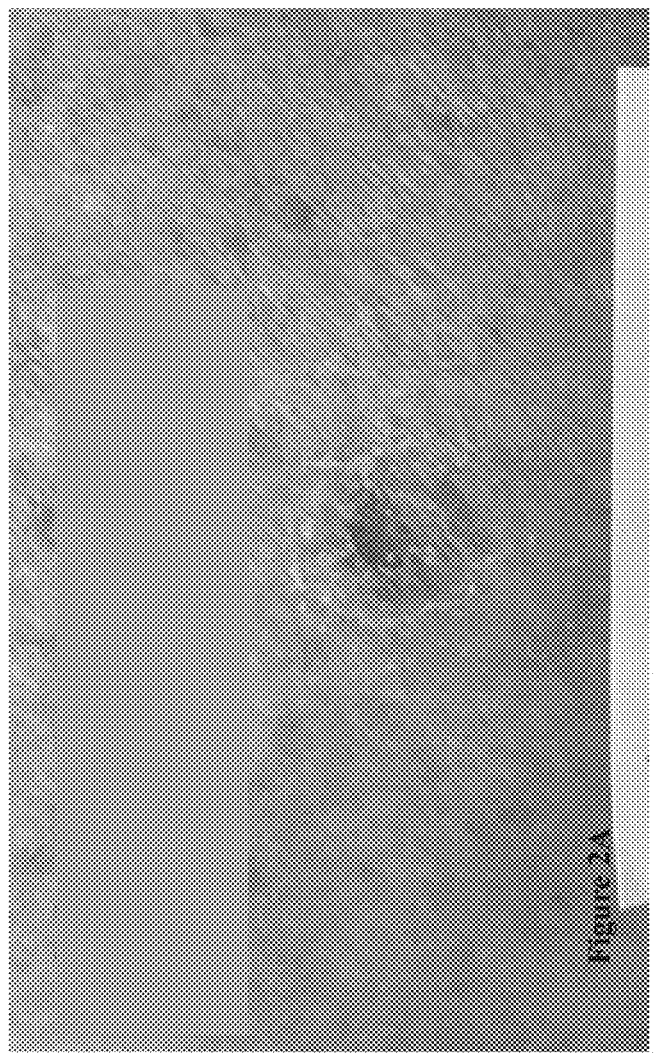
FIG. 2A is a picture of a patient with a nodular BCC lesion before treatment according to specific embodiments of the present invention.
Figure 2B:
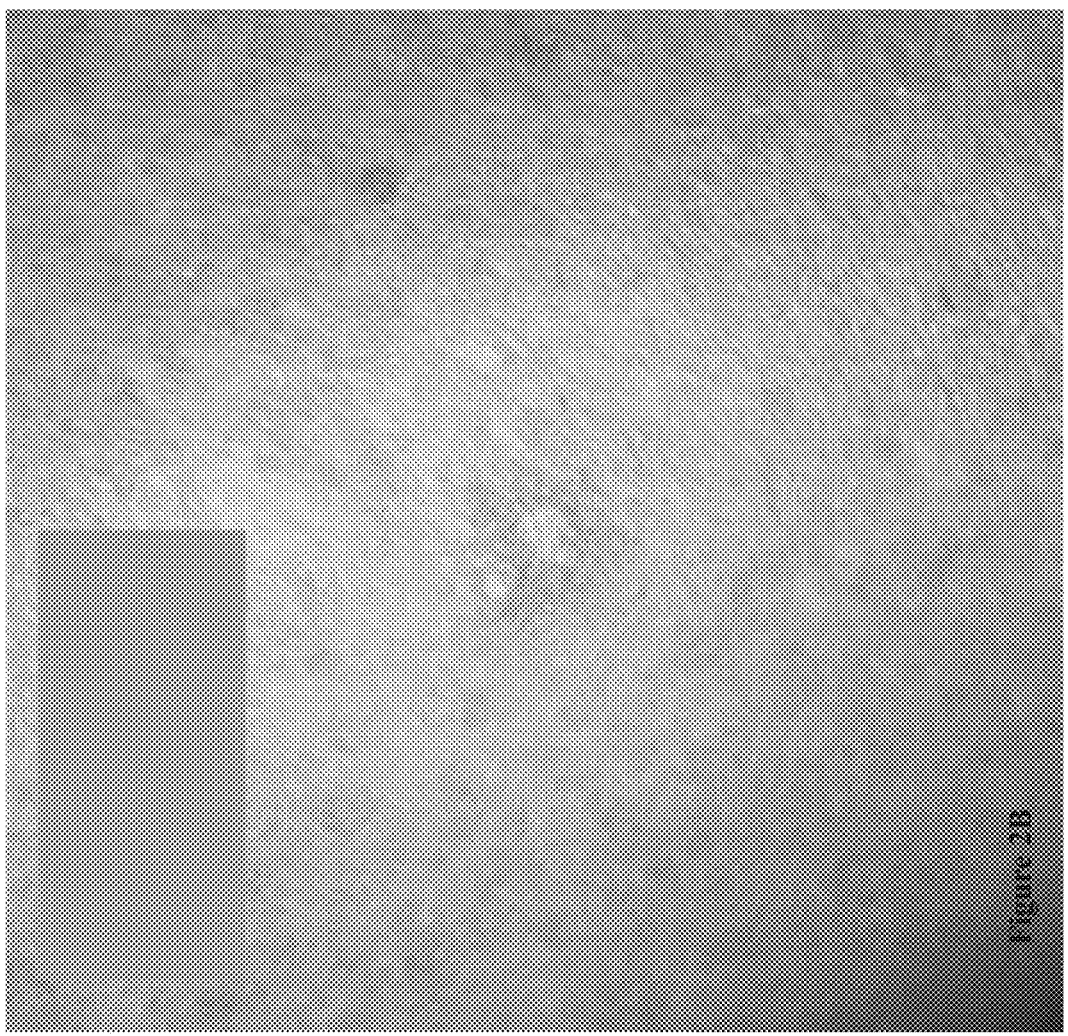
FIG. 2B is a picture of a patient with a nodular BCC lesion after treatment according to specific embodiments of the present invention.

| Before treatment | After treatment |
|---|---|
| FIG. 2A | FIG. 2B |

3
Lesion: SCC in situ on patient's face
Formulation: B, twice daily
Duration of treatment: 7 days

| Before treatment | After treatment |
|---|---|
| FIG. 3A | FIG. 3B |

4
Lesion: BCC on patient's arm
Formulation: B, twice daily
Duration of treatment: 10 days

| Before treatment | After treatment |
|---|---|
| FIG. 4A | FIG. 4B |

5
Lesion: SCC on patient's scalp
Formulation: B, twice daily
Duration of treatment: 10 days

Figure 5A:
FIG. 5A is a picture of a patient with a SCC lesion on a face before treatment according to specific embodiments of the present invention.

| Before treatment | After treatment |
|---|---|
| FIG. 5A | FIG. 5B |

6
Lesion: SCC in situ on patient's face
Formulation: B, twice daily
Duration of treatment: 10 days

| Before treatment | After treatment |
|---|---|
| FIG. 6A | FIG. 6B |

7
Lesion: Superficial BCC on patient's skin
Formulation: B, twice daily
Duration of treatment: 7 days

Figure 7A:
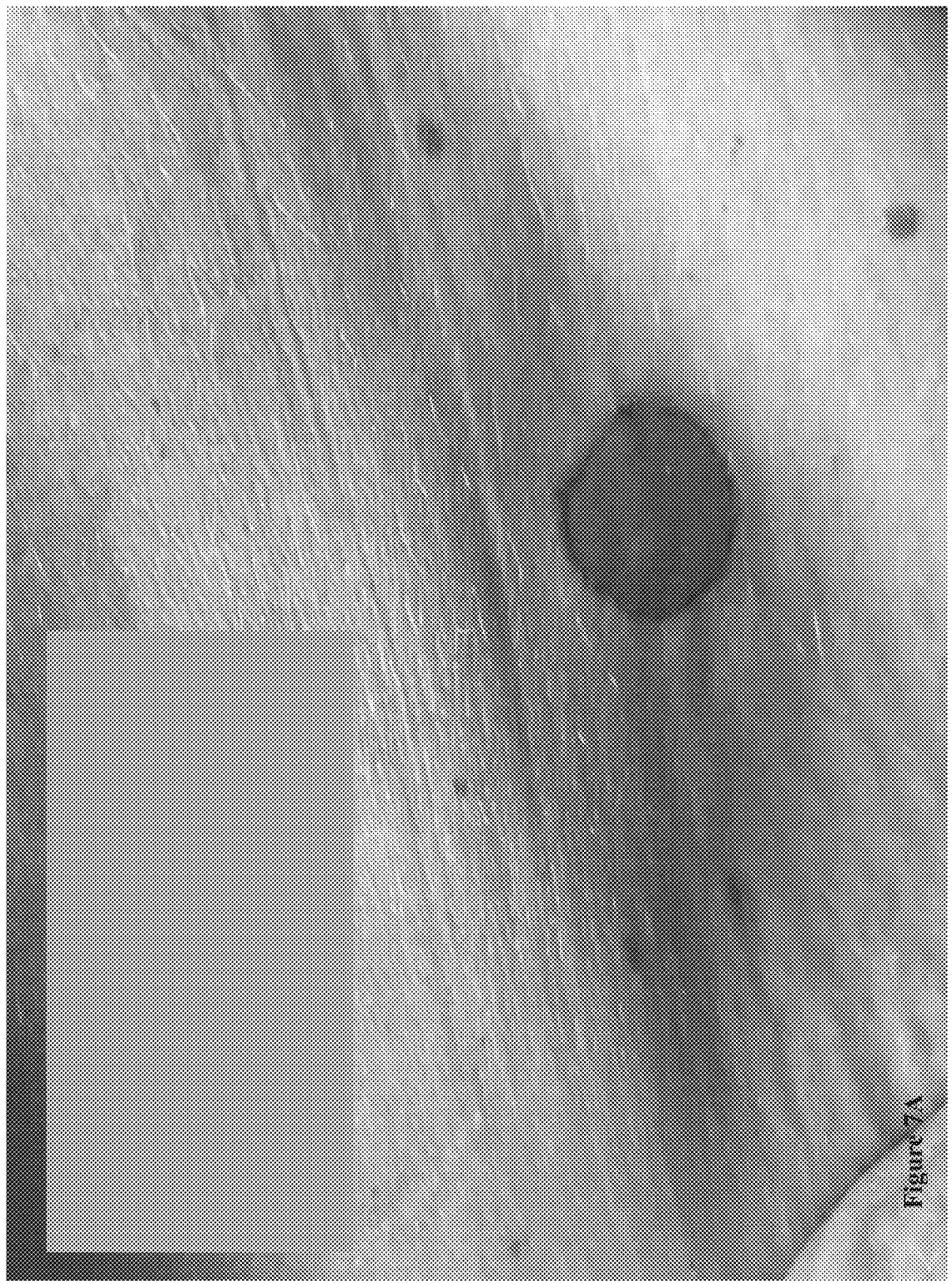
FIG. 7A is a picture of a patient with a superficial BCC lesion during treatment according to specific embodiments of the present invention.
Figure 7B:
FIG. 7B is a picture of a patient with a superficial BCC lesion after treatment according to specific embodiments of the present invention.

| After 10 days of treatment | After treatment |
|---|---|
| FIG. 7A | FIG. 7B |

8
Lesion: SCC in situ on patient's face
Formulation: B, twice daily
Duration of treatment: 10 days

| Before treatment | Day 10 of treatment | After treatment |
|---|---|---|
| FIG. 8A | FIG. 8B | FIG. 8C |

9
Lesion: BCC on patient's neck
Formulation: B, twice daily
Duration of treatment: 10 days

Figure 9C:
FIG. 9C is a picture of a patient with a BCC lesion after treatment according to specific embodiments of the present invention.

| Before treatment | Before treatment | After treatment | After treatment |
|---|---|---|---|
| FIG. 9A | FIG. 9B | FIG. 9C | FIG. 9D |

10
Lesion: SCC in situ
Formulation: B, twice daily
Duration of treatment: 10 days

Figure 10A:
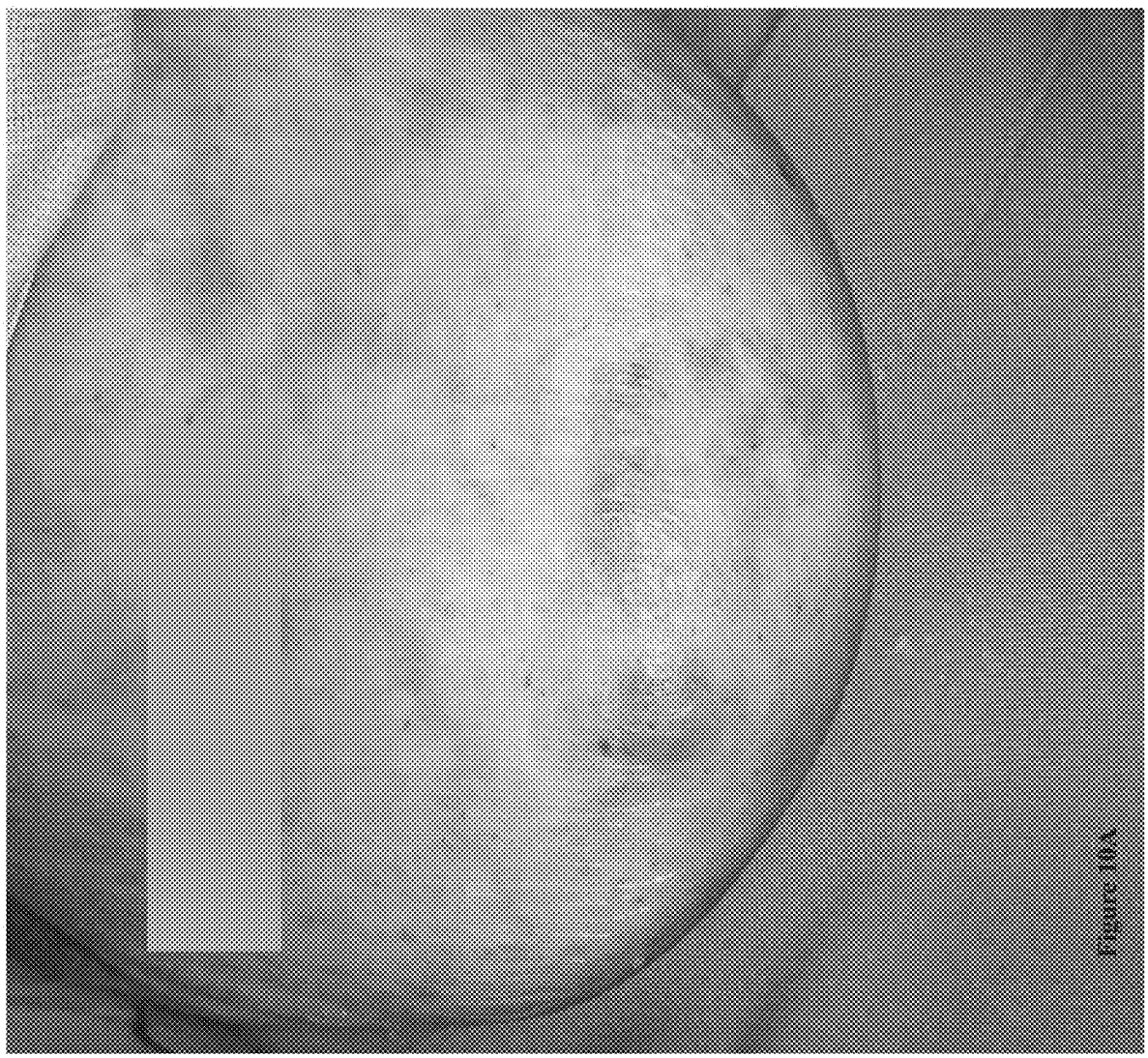
FIG. 10A is a picture of a patient with a SCC in situ lesion before treatment according to specific embodiments of the present invention.
Figure 10D:
FIG. 10D is a picture of a patient with a SCC in situ lesion after treatment according to specific embodiments of the present invention.
Figure 10B:
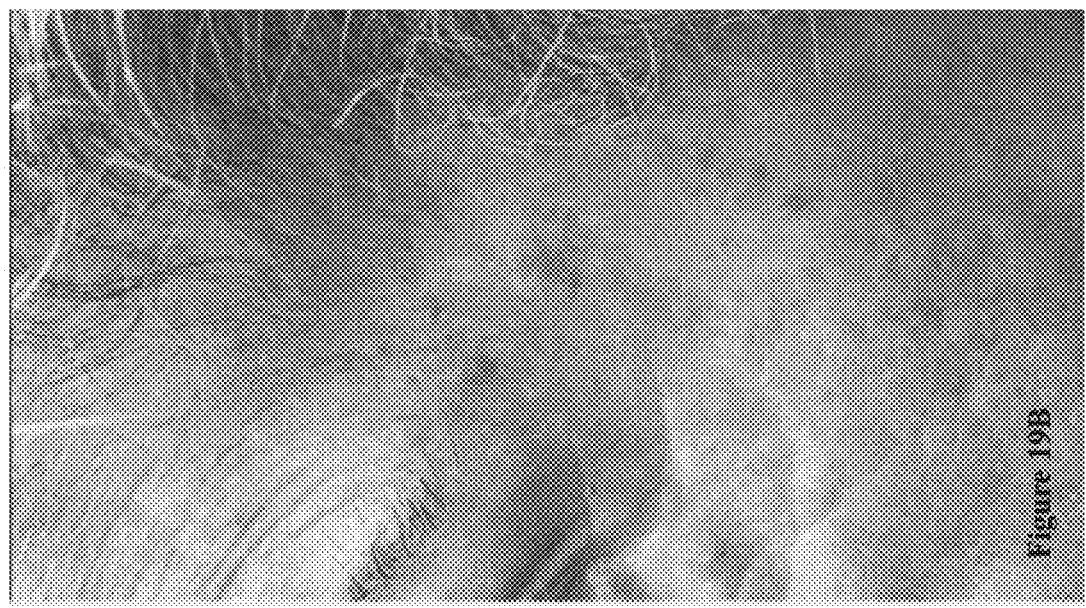
FIG. 10B is a picture of a patient with a SCC in situ lesion during treatment according to specific embodiments of the present invention.

| Before treatment | Day 7 of treatment | After treatment | After treatment |
|---|---|---|---|
| FIG. 10A | FIG. 10B | FIG. 10C | FIG. 10D |

11
Lesion: BCC on on patient's ear
Formulation: B, twice daily
Duration of treatment: 10-14 days

| Before treatment | After treatment |
|---|---|
| FIG. 11A | FIG. 11B |

12
Lesion: BCC on patient's face
Formulation: B, twice daily
Duration of treatment: 10-14 days

Figure 12B:
FIG. 12B is a picture of a patient with a BCC lesion after treatment according to specific embodiments of the present invention.

| Before treatment | After treatment |
|---|---|
| FIG. 12A | FIG. 12B |

13
Lesion: SCC on patient's shin
Formulation: B, twice daily
Duration of treatment: 10-14 days

Figure 13B:
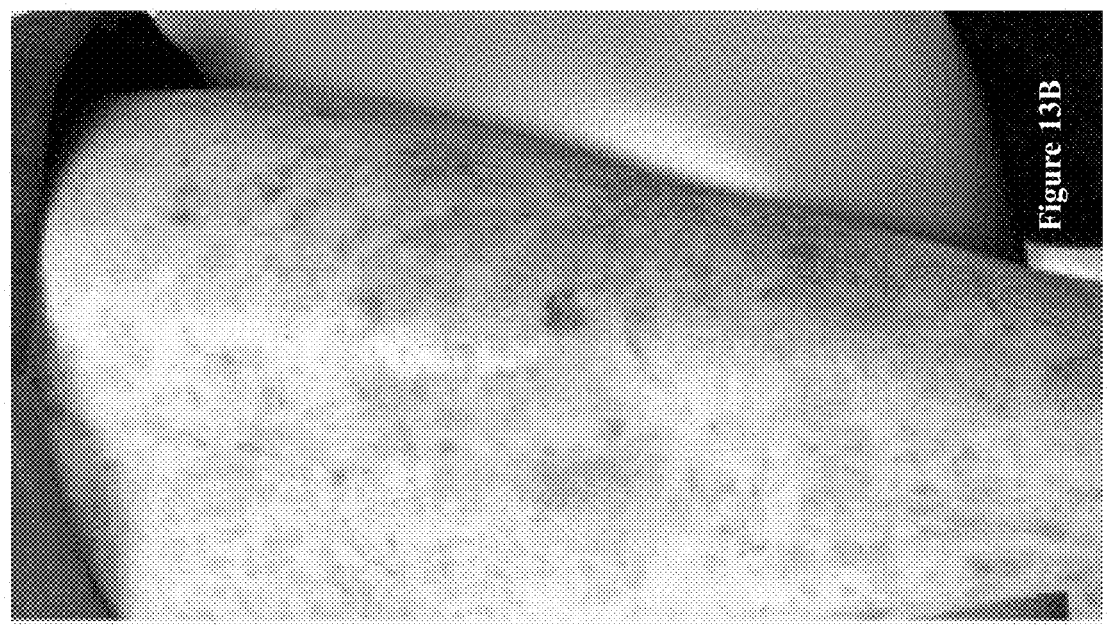
FIG. 13B is a picture of a patient with a SCC lesion on a shin after treatment according to specific embodiments of the present invention.

| Before treatment | After treatment |
|---|---|
| FIG. 13A | FIG. 13B |

14
Lesion: BCC on patient's forehead
Formulation: B, twice daily
Duration of treatment: 10-14 days

Figure 14B:
FIG. 14B is a picture of a patient with a BCC lesion after treatment according to specific embodiments of the present invention.

| Before treatment | After treatment |
|---|---|
| FIG. 14A | FIG. 14B |

15
Lesion: SCC on patient's forehead
Formulation: B, twice daily
Duration of treatment: 10-14 days

| Before treatment | After treatment |
|---|---|
| FIG. 15A | FIG. 15B |

16
Lesion: SCC on patient's ear
Formulation: B, twice daily
Duration of treatment: 10-14 days

| Before treatment | After treatment |
|---|---|
| FIG. 16A | FIG. 16B |

17
Lesion: BCC on patient's ear
Formulation: B, twice daily
Duration of treatment: 10-14 days

| Before treatment | After treatment |
|---|---|
| FIG. 17A | FIG. 17B |

18
Lesion: BCC on patient's arm
Formulation: B, twice daily
Duration of treatment: 10-14 days

Figure 18A:
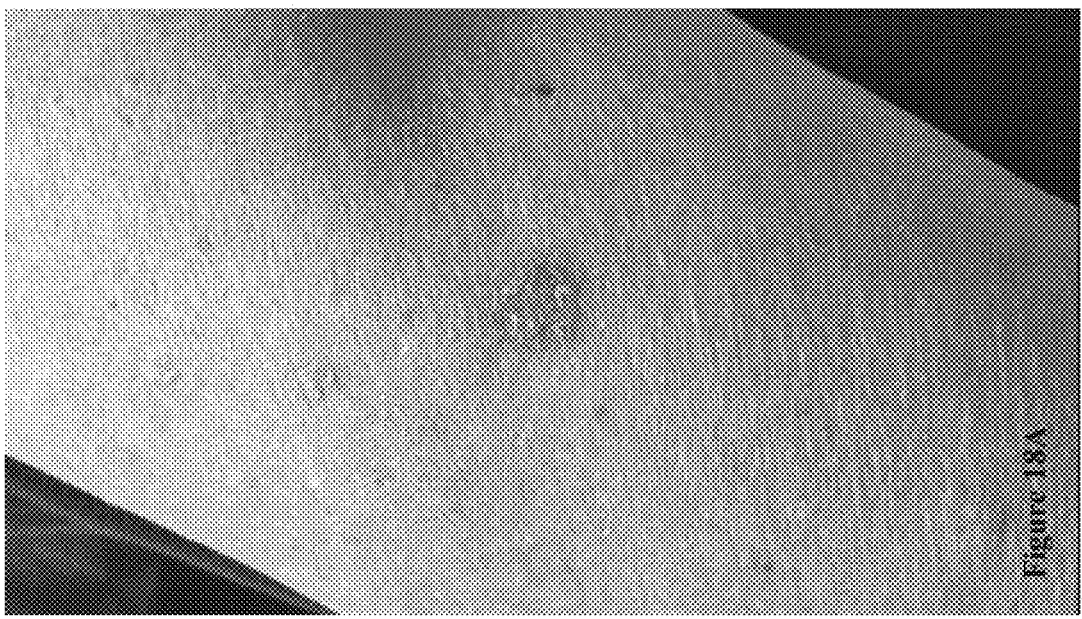
FIG. 18A is a picture of a patient with a BCC lesion on an arm before treatment according to specific embodiments of the present invention.

| Before treatment | After treatment |
|---|---|
| FIG. 18A | FIG. 18B |

19
Lesion: BCC on patient's face
Formulation: B, twice daily
Duration of treatment: 10-14 days

Figure 19A:
FIG. 19A is a picture of a patient with a BCC lesion before treatment according to specific embodiments of the present invention.

| Before treatment | After treatment |
|---|---|
| FIG. 19A | FIG. 19B |

20
Lesion: BCC on patient's face
Formulation: B, twice daily
Duration of treatment: 10-14 days

Figure 20B:
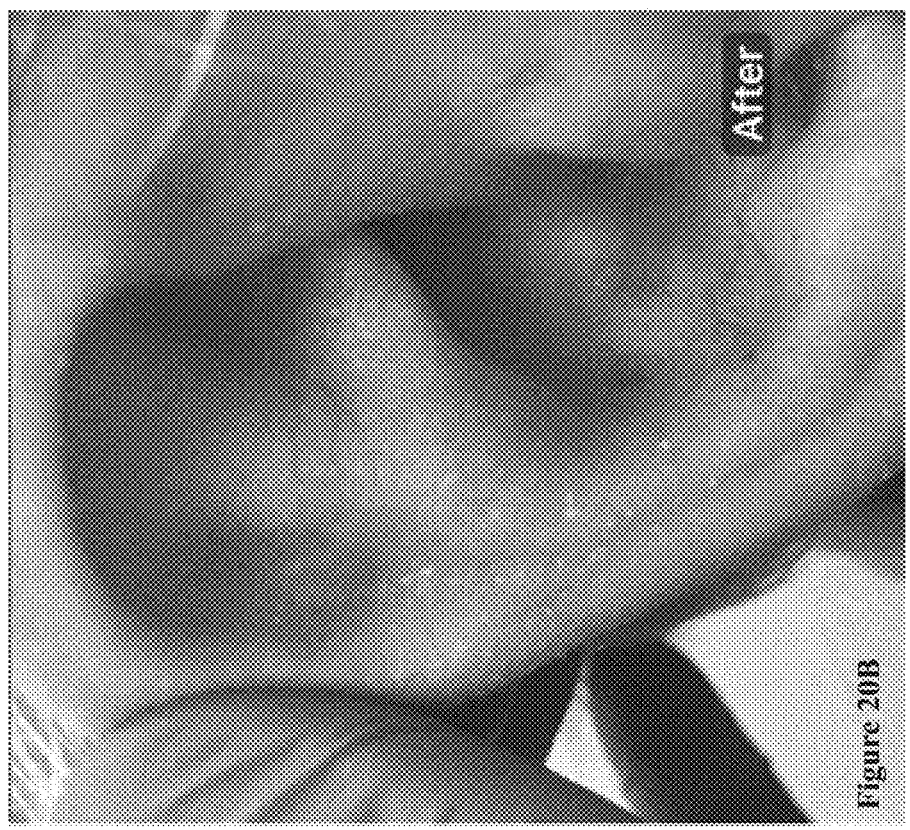
FIG. 20B is a picture of a patient with a BCC lesion after treatment according to specific embodiments of the present invention.

| Before treatment | After treatment |
|---|---|
| FIG. 20A | FIG. 20B |

21
Lesion: BCC on patient's face
Formulation: B, twice daily
Duration of treatment: 10-14 days

| Before treatment | After treatment |
|---|---|
| FIG. 21A | FIG. 21B |

22
Lesion: SCC on patient's arm
Formulation: B, twice daily
Duration of treatment: 10-14 days

Figure 22B:
FIG. 22B is a picture of a patient with a SCC lesion on an arm after treatment according to specific embodiments of the present invention.
Figure 58:
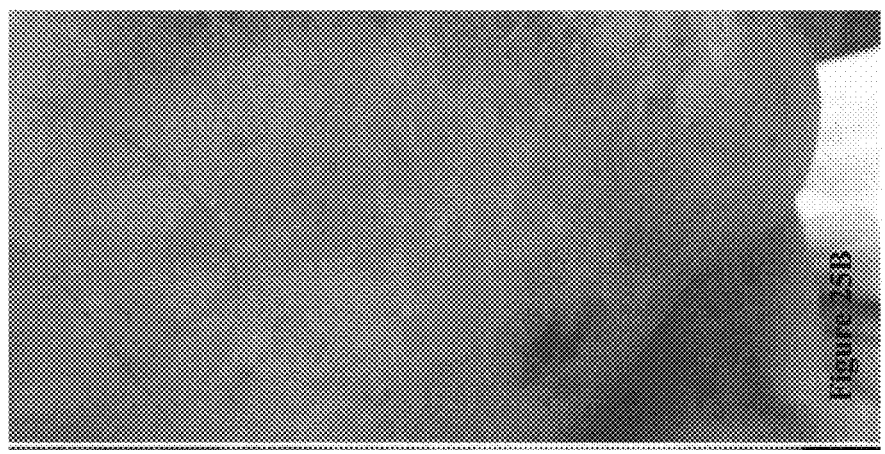

| Before treatment | After treatment |
|---|---|
| FIG. 22A | FIG. 22B |

23
Lesion: SCC on patient's shin
Formulation: B, twice daily
Duration of treatment: 10-14 days

| Before treatment | After treatment |
|---|---|
| FIG. 23A | FIG. 23B |

24
Lesion: SCC on patient's calf
Formulation: B, twice daily
Duration of treatment: 10-14 days

| Before treatment | After treatment |
|---|---|
| FIG. 24A | FIG. 24B |

25
Lesion: BCC on patient's face
Formulation: B, twice daily
Duration of treatment: 10-14 days

| Before treatment | After treatment |
|---|---|
| FIG. 25A | FIG. 25B |

Example 3: Comparative Study in Persons Diagnosed with AK, BCC, SCC and/or SCC In Situ Formulations A and B, as well as the individual active components, or alternative combinations of the active components, will be tested by the inventor. The study will demonstrate the effect of the formulations according to the invention comprising calcipotriene, 5-FU, and diclofenac on pre-cancerous and cancerous skin lesions compared to either the individual components or other combinations of calcipotriene, 5-FU, and diclofenac.

While the present invention has been described with respect to what is presently considered to be the preferred embodiments, it is to be understood that the invention is not limited to the disclosed embodiments. To the contrary, the invention is intended to cover various formulations and methods of treatment included within the spirit and scope of the appended claims. The scope of the following claims is to be accorded the broadest interpretation so as to encompass all such modifications and equivalent structures and functions.

All U.S. and foreign patent documents, all articles, brochures, and all other published documents discussed above are hereby incorporated by reference into the Detailed Description of the Preferred Embodiments.

What is claimed is:

1. A topical composition, wherein the composition comprises:
   a) about 0.5% to about 5% 5-fluorouracil or a salt or hydrate thereof;
   b) about 0.001% to about 0.01% calcipotriene or a salt or hydrate thereof; and
   c) about 1% to about 5% diclofenac or a salt or hydrate thereof.

2. The topical composition of claim 1, wherein the composition is formulated as an ointment, a cream, a lotion, a scalp lotion, a suspension, a powder, a solution, a paste, a spray, an aerosol, an oil, an oil in water emulsion, a liniment or other spreadable liquid or semi liquid preparation.

3. The topical composition of claim 1, wherein the composition is an oil in water emulsion.

4. The topical composition of claim 1, comprising:
   a) about 1% to about 2.5% 5-fluorouracil;
   b) about 0.005% calcipotriene;
   c) about 3% diclofenac sodium;
   d) about 12% to about 17% isopropyl myristate;

e) about 1% to about 3% cetyl alcohol;
f) about 1% to about 3% cetearyl alcohol;
g) about 1% to about 4% polysorbate 60;
h) about 1% to about 4% glyceryl stearate;
i) about 1% to about 4% PEG 100 stearate;
j) about 8% to about 12% propylene glycol;
k) about 2% to about 4% hydroxymethyl aminomethane;
l) about 1% to about 2% hydroxymethyl aminomethane HCl;
m) about 1% to about 3% benzyl alcohol; and
n) purified water.

5. A method of treating a skin lesion, comprising the steps of topically administering an effective amount of a topical composition to an affected area of a subject at least once daily for a period of time that reduces or eliminates the symptoms of that skin lesion in the subject, wherein the topical composition comprises:
   a) about 0.5% to about 5% 5-fluorouracil or a salt or hydrate thereof;
   b) about 0.001% to about 0.01% calcipotriene or a salt or hydrate thereof; and
   c) about 1% to about 5% diclofenac or a salt or hydrate thereof.

6. The method of claim 5, wherein the skin lesion is a cancerous or precancerous skin lesion.

7. The method of claim 6, wherein the cancerous or precancerous skin lesion consists essentially of one or more of the following: basal cell carcinoma, superficial basal cell carcinoma, actinic keratosis, squamous cell carcinoma and squamous cell carcinoma in situ.

8. The method of claim 7, wherein the period of time is 7 to 14 consecutive days.

9. A method of treating a precancerous or cancerous skin lesion comprising the steps of topically administering to an affected area an effective amount of a topical composition for a period of time that results in reduction or elimination of the skin condition, the topical composition comprising:
   a) about 1% to about 2.5% 5-fluorouracil or a salt or hydrate thereof;
   b) about 0.005% calcipotriene or a salt or hydrate thereof; and
   c) about 3% diclofenac or a salt or hydrate thereof;
   wherein the precancerous or cancerous skin lesion consists essentially of one or more of the following: basal cell carcinoma, superficial basal cell carcinoma, actinic keratosis, squamous cell carcinoma and squamous cell carcinoma in situ.

10. The method of claim 9, wherein the period of time is at least once daily for at least 7 days.

11. The method of claim 7, wherein the administration results in at least an 85% reduction in the respective lesion on the affected skin.

12. The method of claim 9, wherein the administration results in at least an 85% reduction in the respective lesion on the affected skin.

13. The method of claim 5, wherein the effective amount is about 0.1 to about 100 mg of the composition.

14. The topical composition of claim 1, further comprising cetyl alcohol and isopropyl myristate.

15. The topical composition of claim 1, further comprising isopropyl myristate, cetyl alcohol, polysorbate 60, glyceryl stearate, PEG 100 stearate, and cetearyl alcohol.

* * * * *